USOO5705491A

United States Patent [19]
Yamada

[11] Patent Number: 5,705,491
[45] Date of Patent: Jan. 6, 1998

[54] ADENOSINE DEAMINASE INHIBITOR

[75] Inventor: Toshio Yamada, Hyogo, Japan

[73] Assignee: Nippon Zoki Pharmaceutical Co., Ltd., Osaka, Japan

[21] Appl. No.: 141,597

[22] Filed: Oct. 27, 1993

[30] Foreign Application Priority Data

Oct. 27, 1992 [JP] Japan .................. 4-312764
Oct. 27, 1992 [JP] Japan .................. 4-312765

[51] Int. Cl.$^6$ .................. A61K 31/70; C07H 19/167
[52] U.S. Cl. .................. 514/46; 536/21.62; 536/27.63; 536/27.7
[58] Field of Search .................. 514/46; 536/27.62, 536/27.63, 27.7

[56] References Cited

U.S. PATENT DOCUMENTS

| | | | |
|---|---|---|---|
| 4,843,066 | 6/1989 | Yamada et al. | 514/46 |
| 4,985,409 | 1/1991 | Yamada et a. | 514/46 |

FOREIGN PATENT DOCUMENTS

| | | |
|---|---|---|
| 0 181 129 A3 | 5/1986 | European Pat. Off. . |
| 0 219 876 A2 | 4/1987 | European Pat. Off. . |
| 0 269 574 A2 | 6/1988 | European Pat. Off. . |
| 0 378 518 A2 | 7/1990 | European Pat. Off. . |
| 0 490 818 A1 | 6/1992 | European Pat. Off. . |
| 63-239294 | 10/1988 | Japan . |
| 2-184696 | 7/1990 | Japan . |
| 2-218689 | 8/1990 | Japan . |
| 2 226 027 | 6/1990 | United Kingdom . |
| WO 88/03147 | 5/1988 | WIPO . |
| WO 92/0517 | 4/1992 | WIPO . |

OTHER PUBLICATIONS

The 1991 Sigma Chemical Company Catalog, St. Louis, Missouri, pp. 41 and 660.
Chemical Abstract vol. 66, No. 3, Abstr. No. 8441c, Rockwell et al. Mol. Pharmacol. 2(6):574–584, 1966.
J. G. Niedzwicki, et al., "Structure–Activity Relationship of Ligands of Human Plasma Adenosine Deaminase$_2$", *Biochemical Pharmacology*, vol. 41, No. 11, 1991, pp. 1615–1624.
Phillis, et al., "Brian Adenosine and Transmitter Amino Acid Release from the Ischemic Rat Cerebral Cortex: Effects of the Adenosine Deaminase Inhibitor Deoxycoformycin", *Journal of Neurochemistry*, vol. 56, No. 2, pp. 644–650 (1991).
Cristalli, et al., "Adenosine Deaminase Inhibitors: Synthesis and Structure–Activity Relationship of 2–Hydroxy–3–nonyl Derivatives of Azoles", *J. Med. Chem.*, vol. 37, pp. 201–205 (1994).
Zhu, et al., "Protective Effects of an adenosine deaminase inhibitor on ischemia–reperfusion injury in isolated perfused rat heart", *Am. J. Physiol.*, vol. 259, H835–H838 (1990).
Kato, et al., "Effects of Antiasthma Drugs on Superoxide Anion Generation from Human Polymorphonuclear Leukocytes or Hypoxanthine–Xanthine Oxidase System", *Int. Arch. Allergy Appl. Immunol.*,vol. 96, pp. 128–133 (1991).

Rockwell, et al., "Studies on Adenosine Deaminase I. Purification and Properties of Ox Heart Adenosine Deaminase," *Mol. Pharmacol.* 2, 574–584 (1966).

*Primary Examiner*—Gary L. Kunz
*Attorney, Agent, or Firm*—Fisher, Christen & Sabol

[57] ABSTRACT

The present invention relates to adenosine deaminase inhibitors containing at least one O-alkylated moiety and the pharmaceutically acceptable salts thereof.

The pharmaceutical compositions of the present invention include adenosine deaminase inhibitors containing at least one of the compounds represented by Formula (I):

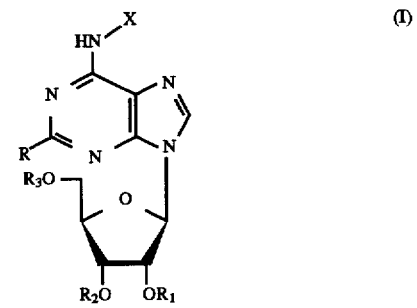

wherein each of $R_1$, $R_2$, and $R_3$ are the same or different and is hydrogen or alkyl;

R is hydrogen, alkyl, alkenyl, alkynyl, hydroxyalkynyl, alkoxy, phenyl, hydroxy, amino, alkylamino, phenylamino or halogen;

X is hydrogen, alkyl, alkynyl, allyl, methallyl, cycloalkyl, alkyl having one or more hydroxy groups, phenyl, substituted phenyl, alkyl having one or more phenyl groups, alkyl having one or more substituted phenyl groups, bicycloalkyl, naphthylalkyl, acenaphthylenylalkyl or a compound represented by Formula (II) or Formula (III)

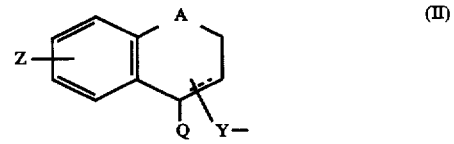

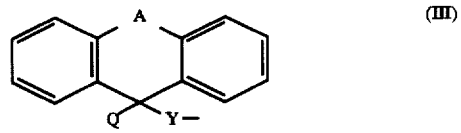

wherein Z is hydrogen, hydroxy or lower alkoxy;

Q is hydrogen or hydroxy;

A is —CH$_2$—, —O—, —S— or a mere linkage;

Y is (CH$_2$)$_n$— or a mere linkage;

n is an integer from 1 to 3; and any of $R_1$, $R_2$, and $R_3$ is $R_3$ lower alkyl.

13 Claims, No Drawings

ADENOSINE DEAMINASE INHIBITOR

FIELD OF THE INVENTION

The present invention relates to adenosine deaminase inhibitors containing at least one O-alkylated moiety and the pharmaceutically acceptable salts thereof.

BACKGROUND OF THE INVENTION

Adenosine deaminase is an enzyme producing inosine by deamination of adenosine in vivo and is prevalent in animals and microorganisms. When adenosine deaminase is inhibited, the adenosine concentration in tissues is increased while the inosine concentration is decreased whereupon endogenous inactivation of adenosine is inhibited. When the tissue is in an ischemic state, neutrophils produce activated oxygen and adenosine inhibits this oxygen production. In addition, adenosine directly eliminates the produced activated oxygen. Further, as a result of a decrease in the inosine concentration, the supply of hypoxanthine is decreased. Hypoxanthine is a substrate in the xanthine-xanthineoxidase system. The xanthine-xanthineoxidase system is one of the systems producing the activated oxygen. It has been known that adenosine deaminase inhibitors, which inhibit the production of such activated oxygen sources and also eliminate them, exhibit pharmacological actions such as improvement of coronary and cerebral blood vessel circulation, prevention and therapy of renal diseases, and antiinflammatory activity.

It has been found that the O-alkylated adenosine derivatives of the instant invention exhibit excellent adenosine deaminase inhibiting action.

SUMMARY OF THE INVENTION

The present invention pertains to adenosine deaminase inhibitors containing at least one O-alkylated moiety and the pharmaceutically acceptable salts thereof.

The pharmaceutical compositions of the present invention include adenosine deaminase inihibitors containing at least one of the compounds represented by Formula (I):

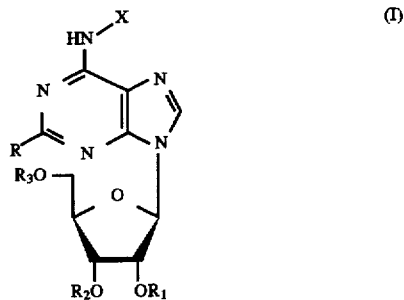

wherein each of $R_1$, $R_2$, and $R_3$ are the same or different and is hydrogen or alkyl;

R is hydrogen, alkyl, alkenyl, alkynyl, hydroxyalkynyl, alkoxy, phenyl, hydroxy, amino, alkylamino, phenylamino or halogen;

X is hydrogen, alkyl, alkynyl, allyl, methallyl, cycloalkyl, alkyl having one or more hydroxy groups, phenyl, substituted phenyl, alkyl having one or more phenyl groups, alkyl having one or more substituted phenyl groups, bicycloalkyl, naphthylalkyl, acenaphthylenylalkyl or a compound represented by Formula (II) or Formula (III)

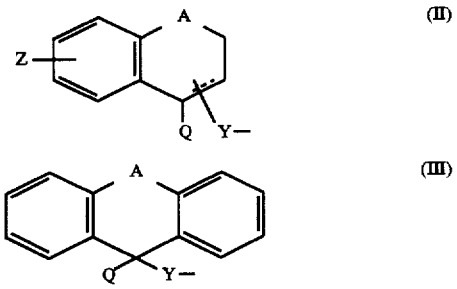

wherein Z is hydrogen, hydroxy or lower alkoxy;

Q is hydrogen or hydroxy;

A is $-CH_2-$, $-O-$, $-S-$ or a single bond forming a five-membered ring;

Y is $(CH_2)_n-$ or a single bond;

n is an integer from 1 to 3; and at least one of $R_1$, $R_2$, and $R_3$ is alkyl, such as a lower alkyl.

The compounds represented by Formula (I) are present in the adenosine deaminase inhibitors in a pharmaceutically effective amount.

The compounds of the present invention having adenosine deaminase inhibiting action are useful pharmaceutical compositions for the prevention and therapy of various kinds of diseases. Such diseases include ischemic heart diseases, diseases caused by cerebrovascular disorder, renal diseases and allergic diseases. Moreover, the compounds of the present invention are very useful pharmaceutical compositions for the prevention and therapy of post-operative complicated diseases because they inactivate activated oxygen which is generated in ischemic areas during the recirculation of blood after operations.

The compounds of the instant invention may also be administered before or together with aniticancer drugs and/or antiviral drugs.

DETAILED DESCRIPTION OF THE INVENTION

The present invention relates to adenosine deaminase inhibitors containing a pharmaceutically effective amount of at least one of the compounds represented by the following general formula (I) or pharmaceutically acceptable salts thereof.

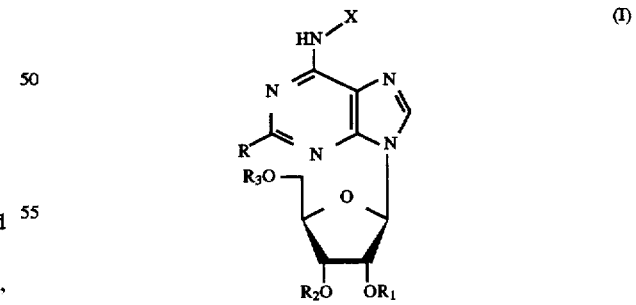

In Formula (I) each of $R_1$, $R_2$ and $R_3$ may be the same or different and is hydrogen or alkyl; R is hydrogen, alkyl, alkenyl, alkynyl, hydroxyalkynyl, alkoxy, phenyl, hydroxy, amino, alkylamino, phenylamino or halogen; X is hydrogen, alkyl, alkynyl, allyl, methallyl, cycloalkyl, alkyl having one or more hydroxy groups, phenyl, substituted phenyl, alkyl having one or more phenyl groups, alkyl having one or more substituted phenyl groups, bicycloalkyl, naphthylalkyl, acenaphthylenylalkyl or a group represented by the following general formulae (II) or (III):

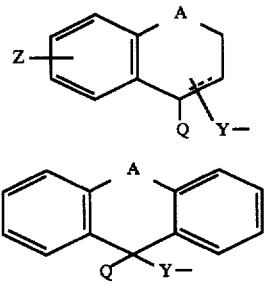

Z is hydrogen, hydroxy or lower alkoxy; Q is hydrogen or hydroxy; A is —$CH_2$—, —O—, —S— or a single bond forming a five-membered ring; Y is —$(CH_2)_n$— or a single bond; n is an integer from 1 to 3 and at least one of $R_1$, $R_2$ and $R_3$ is an alkyl group.

A substituted phenyl or a substituted phenyl group is defined, for the purposes of this invention, as including a phenyl which has been substituted with one or more halogen, lower alkyl, lower alkoxy and/or trifluoromethyl substituents. In Formula (II), a broken line symbolizes the presence of either a double bond or a single bond.

In the above general formula (I), each of $R_1$, $R_2$ and $R_3$ may be the same or different and is hydrogen or alkyl. Preferably, $R_1$ is a hydrogen or a linear or branched alkyl having 1 to 10 carbons. Exemplary alkyl groups include methyl, ethyl, propyl, isopropyl, butyl, isobutyl, sec-butyl, tert-butyl, pentyl, isopentyl, neopentyl, tert-pentyl, hexyl, dimethylbutyl, heptyl, octyl, nonyl and decyl. $R_2$ and $R_3$ are hydrogen or linear or branched alkyl having 1 to 4 carbons. Examples of such alkyl groups include methyl, ethyl, propyl, isopropyl, butyl, isobutyl, sec-butyl and tert-butyl. In a preferred embodiment, $R_3$ is hydrogen. At least one of $R_1$, $R_2$ and $R_3$ must be an alkyl.

R is hydrogen, alkyl, alkenyl, alkynyl, hydroxyalkynyl, alkoxy, phenyl, hydroxy, amino, alkylamino, phenylamino, or halogen. Preferred alkyl groups are linear or branched alkyls having 1 to 20 carbons. Exemplary alkyl groups include methyl, ethyl, propyl, isopropyl, butyl, isobutyl, sec-butyl, tert-butyl, pentyl, isopentyl, neopentyl, tert-pentyl, hexyl, dimethylbutyl, heptyl, octyl, nonyl, decyl and stearyl.

Preferred alkenyl groups are linear or branched alkenyls having 2 to 4 carbons. Exemplary alkenyl groups are ethenyl, 1-propenyl, 2-propenyl, 1-butenyl, 2-butenyl and 3-butenyl.

Preferably the alkynyl is a linear or branched alkynyl having 2 to 20 carbons. Exemplary alkynyl groups include ethynyl, 1-propynyl, 2-propynyl, 1-butynyl, 2-butynyl, 3-butynyl, sec-butynyl, pentynyl, isopentynyl, 2-pentynyl, 3-pentynyl, 4-pentynyl, hexynyl, heptynyl, octynyl, nonynyl, decynyl and stearynyl.

If R is a hydroxyalkynyl, it is preferred that the alkynyl is substituted with one or more hydroxy groups.

Preferred alkoxy groups include linear or branched alkoxy having 1 to 4 carbons. Examples of such groups include methoxy, ethoxy, propoxy, isopropoxy, butoxy, isobutoxy, sec-butoxy, and tert-butoxy.

Preferred alkylamino groups include linear or branched alkylamino groups having 1 to 10 carbons. Examples of such groups include methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, dimethylbutylamino, heptylamino, octylamino, nonylamino and decylamino.

Exemplary halogen groups include fluoro, chloro, bromo, and iodo.

X is hydrogen, alkyl, alkynyl, allyl, methallyl, cycloalkyl, alkyl having one or more hydroxy groups, phenyl, substituted phenyl, alkyl having one or more phenyl groups, alkyl having one or more substituted phenyl groups, bicycloalkyl, naphthylalkyl, acenaphthylenylalkyl or a compound represented by Formula (II) or Formula (III). The substituted phenyl groups include a phenyl which has been substituted with one or more halogen, lower alkyl, lower alkoxy and/or trifluoromethyl substituents.

Preferred alkyl groups are linear or branched alkyls having 1 to 6 carbons. Exemplary alkyl groups include methyl, ethyl, propyl, isopropyl, butyl, isobutyl, sec-butyl, tert-butyl, pentyl, isopentyl, neopentyl, tert-pentyl, hexyl and dimethylbutyl.

Preferred alkynyl groups are linear or branched alkynyls having 2 to 7 carbons. Examples of such groups include ethynyl, 1-propynyl, 2-propynyl, 1-butynyl, 2-butynyl, 3-butynyl, sec-butynyl, pentynyl, isopentynyl, 2-pentynyl, 3-pentynyl, 4-pentynyl, hexynyl and heptynyl.

Preferred cycloalkyl groups have 3 to 8 carbons. Examples of such groups include cyclopropyl, cyclobutyl, cyclopentyl, cyclohexyl, cycloheptyl, and cyclooctyl.

Preferred alkyl groups having one or more hydroxy substituents are linear or branched alkyls having 1 to 4 carbons. Examples of such groups include methyl, ethyl, propyl, isopropyl, butyl, isobutyl, sec-butyl and tert-butyl substituted with one or two hydroxy groups.

Preferred alkyl groups having one or more phenyl or substituted phenyl substituents are phenylalkyl or diphenylalkyl in which one or two substituted phenyl as defined above is/are bonded to a linear or branched alkyl having 1 to 3 carbons. Examples of such alkyl groups are methyl, ethyl, propyl, and isopropyl.

Preferred bicycloalkyl groups are endo- or exo-bicyclo [2,2,1]heptyl.

Preferred naphthylalkyls are those in which the naphthyl group is bonded to an alkyl having 1 to 3 carbons. Examples of such alkyl groups are methyl, ethyl, propyl and isopropyl.

Preferred acenaphthylenylalkyls are those in which acenaphthylenyl is bonded to an alkyl having 1 to 3 carbons. Examples of such alkyl groups are methyl, ethyl, propyl and isopropyl. It should be noted that the 1,2-dihydro form of an acenaphthylenylalkyl may also be used within the context of the instant invention. X may also be a group represented by either Formula (II) or Formula (III).

In a preferred embodiment, X is either hydrogen or an alkyl having 1 to 3 carbons.

In the general formulae (II) and (III), Z is hydrogen, hydroxy or lower alkoxy. Preferably Z is a linear or branched alkoxy having 1 to 3 carbons. Exemplary alkoxy groups are methoxy, ethoxy, propoxy and isopropoxy. Q is hydrogen or hydroxy. A is —$CH_2$—, —O—, —S— or a single bond forming a five-membered ring; Y is —$(CH_2)_n$— or a single bond; and n is an integer from 1 to 3. In Formula (II) a broken line symbolizes the presence of either a single bond or a double bond.

When A is a single bond forming a five-membered ring the following groups result:

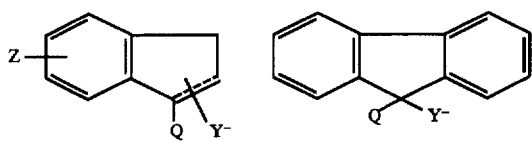

When Y is a single bond the following groups result:

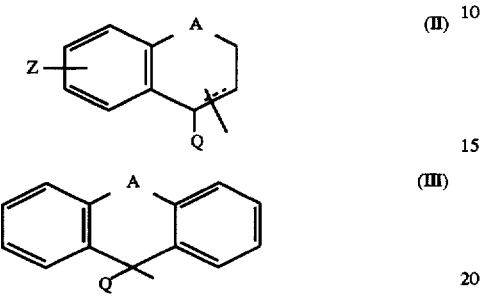

The adenosine derivatives of the present invention include the following novel compounds:

(1) Adenosine derivatives represented by the following general formula (Ia):

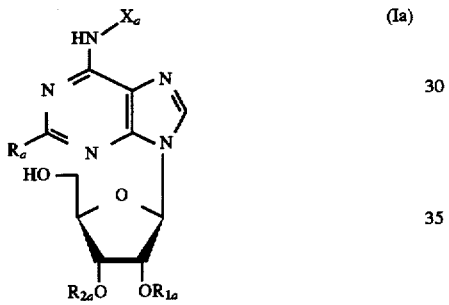

wherein each of $R_1a$, $R_2a$ and Xa may be the same or different and is hydrogen or alkyl;

Ra is an alkyl having more than 6 carbon atoms, alkenyl, alkynyl, hydroxyalkynyl, alkoxy, phenyl, hydroxy, alkylamino or phenylamino; and at least one of $R_1a$ and $R_2a$ is alkyl.

(2) Adenosine derivatives represented by the following general formula (Ib):

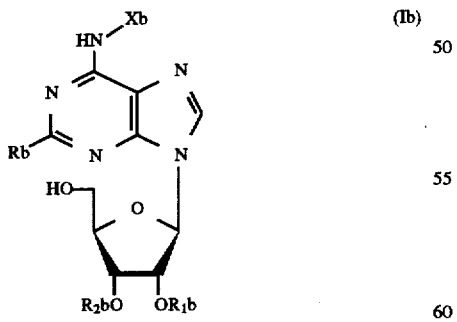

wherein each of $R_1b$ and $R_2b$ may be the same or different and is alkyl;

Rb and Xb is hydrogen or alkyl; and at least one of Rb and Xb is an alkyl.

(3) Adenosine derivatives represented by the following general formula (Ic):

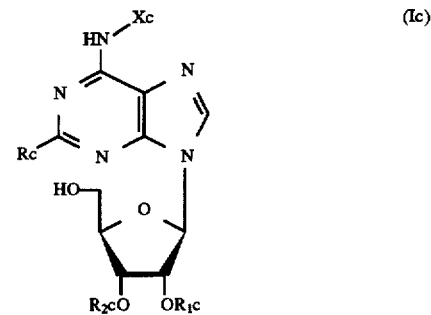

wherein each of $R_1c$, $R_2c$ and Xc may be the same or different and is hydrogen or an alkyl;

Rc is bromo or iodo; and at least one of $R_1c$ and $R_2c$ is an alkyl.

(4) Adenosine derivatives represented by the following general formula (Id):

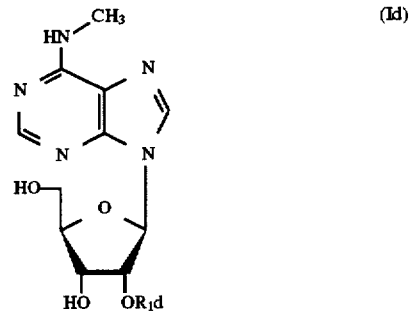

wherein $R_1d$ is an alkyl having more than 2 carbons.

Preferred substituents in the said adenosine derivatives represented by formulae (Ia) to (Id) are the same groups indicated in the formula (I).

Examples of the compound which is contained as an effective component in the adenosine deaminase inhibitor in accordance with the present invention are as follows:

(Compound 1) 2'-O-Methyladenosine;
(Compound 2) 3'-O-Methyladenosine;
(Compound 3) 2'-O-Ethyl adenosine;
(Compound 4) 2'-O-n-Butyladenosine;
(Compound 5) 2,2'-O-Dimethyl adenosine;
(Compound 6) 2,3'-O-Dimethyl adenosine;
(Compound 7) 2-Isopropyl-2'-O-methyladenosine;
(Compound 8) 2-Isopropyl-3'-O-methyladsnosine;
(Compound 9) 2-Methoxy-3'-O-methyladsnosine;
(Compound 10) 2-Methyl-2'-O-ethyl adenosine;
(Compound 11) 2-Methyl-2'-O-n-butyl adenosine;
(Compound 12) 5'-O-Methyl adenosine;
(Compound 13) 5'-O-n-Butyl adenosine;
(Compound 14) 2',5'-O-Dimethyladenosine;
(Compound 15) 3',5'-O-Dimethyl adenosine;
(Compound 16) 2,5'-O-Dimethyl adenosine;
(Compound 17) 2-Methyl-5'-O-n-butyladenosine;
(Compound 18) $N^6$,2'-O-Dimethiladenosine;
(Compound 19) $N^6$-Ethyl-2'-O-methyladenosine;
(Compound 20) $N^6$-n-Butyl-2'-O-methyladenosine;
(Compound 21) $N^6$-Methyl-2'-O-ethyladenosine;
(Compound 22) $N^6$-Methyl-2'-O-n-butyladenosine;
(Compound 23) $N^6$-Methyl-2'-O-n-hexyladenosine;
(Compound 24) $N^6$-Methyl-2'-O-n-octyladenosine;
(Compound 25) $N^6$, 5'-O-Dimethyladenosine;
(Compound 26) $N^6$-n-Butyl-5'-O-methyladenosine;
(Compound 27) 2, $N^6$,2'-O-Trimethyladenosine;

(Compound 28) 2, $N^6$-Dimethyl-2'-O-ethyladenosine;
(Compound 29) $N^6$-n-Butyl-2,2'-O-dimethyladenosine;
(Compound 30) $N^6$,2'-O-Dimethyl-2-hexyladenosine;
(Compound 31) $N^6$,2'-O-Dimethyl-2-decyladenosine;
(Compound 32) $N^6$,2'-O-Dimethyl-2-(1-hexyn-1-yl)-adenosine;
(Compound 33) $N^6$,2'-O-Dimethyl-2-(1-dodecyn-1-yl)-adenosine;
(Compound 34) 2,$N^6$,5'-O-Trimethyladenosine;
(Compound 35) $N^6$-n-Butyl-2,5'-O-dimethyladenosine;
(Compound 36) 2,$N^6$,3'-O-Trimethyladenosine;
(Compound 37) 2-Phenyl-2'-O-methyladenosine;
(Compound 38) 2-Phenyl-3'-O-methyladenosine;
(Compound 39) 2-Hydroxy-2'-O-methyladenosine;
(Compound 40) 2-Hydroxy-3'-O-methyladenosine;
(Compound 41) 2-Chloro-2'-O-methyladenosine;
(Compound 42) 2-Chloro-3'-O-methyladeonsine;
(Compound 43) 2-Bromo-2'-O-methyladenosine;
(Compound 44) 2-Bromo-3'-O-methyladeonsine;
(Compound 45) 2-Bromo-$N^6$,2'-O-dimethyladenosine;
(Compound 46) 2-Bromo-$N^6$,3'-O-dimethyladeonsine;
(Compound 47) 2-Iodo-2'-O-methyladenosine;
(Compound 48) 2-Iodo-3'-O-methyladeonsine;
(Compound 49) 2-Fluoro-2'-O-methyladenosine;
(Compound 50) 2-Amino-2'-O-methyladenosine;
(Compound 51) 2-Amino-3'-O-methyladenosine;
(Compound 52) 2-Pentylamino-2'-O-methyladenosine;
(Compound 53) 2-Phenylamino-2'-O-methyladenosine;
(Compound 54) 2-Phenylamino-3'-O-methyladenosine;
(Compound 55) 2-Phenylamino-$N^6$,2'-O-dimethyladenosine;
(Compound 56) 2-Phenylamino-$N^6$,3'-O-dimethyladenosine;
(Compound 57) 2-(3-Hydroxy-1-propyn-1-yl)-2'-O-methyladenosine;
(Compound 58) 2-(3-Hydroxy-1-propyn-1-yl)-3'-O-methyladenosine;
(Compound 59) 2',3'-O-Dimethyladenosine;
(Compound 60) $N^6$,2',3'-O-Trimethyladenosine;
(Compound 61) $N^6$-Methyl-2',3'-O-diethyladenosine;
(Compound 62) $N^6$-n-Butyl-2',3'-O-dimethyladenosine;
(Compound 63) 2,2',3'-O-Trimethyladenosine;
(Compound 64) 2,$N^6$,2',3'-O-Tetramethyladenosine;
(Compound 65) $N^6$-Allyl-2'-O-methyladenosine;
(Compound 66) $N^6$-Methallyl-2'-O-methyladenosine;
(Compound 67) $N^6$-(2,3-Dihydroxypropyl)-2'-O-methyladenosine;
(Compound 68) $N^6$-Cyclopropyl-2'-O-methyladenosine;
(Compound 69) $N^6$-Cyclopentyl-2'-O-methyladenosine;
(Compound 70) $N^6$-Cyclopentyl-2'-O-ethyladenosine;
(Compound 71) $N^6$-Cyclopentyl-2,2'-dimethyladenosine;
(Compound 72) $N^6$-Cyclopentyl-2-bromo-2'-O-methyladenosine;
(Compound 73) $N^6$-Cyclohexyl-2'-O-methyladenosine;
(Compound 74) $N^6$-Cyclohexyl-2,2'-O-dimethyladenosine;
(Compound 75) $N^6$-Cycloheptyl-2'-O-methyladenosine;
(Compound 76) $N^6$P-Methoxyphenyl-2'-O-methyladenosine;
(Compound 77) $N^6$-P-Fluorophenyl-2'-O-methyladenosine;
(Compound 78) $N^6$P-Chlorophenyl-2'-O-methyladenosine;
(Compound 79) $N^6$Benzyl-2'-O-methyladenosine;
(Compound 80) $N^6$-(R)-Phenyl-isopropyl-2'-O-methyladenosine;
(Compound 81) $N^6$-(2,2-Diphenylethyl)-2'-O-methyladenosine;
(Compound 82) $N^6$-(exo-Dicyclo[2,2,1]heptyl)-2'-O-methyl-adenosine;
(Compound 83) $N^6$-(endo-Dicyclo[2,2,1]heptyl)-2'-O-methyladenosine;
(Compound 84) $N^6$-(1-Naphthyl)methyl-2'-O-methyladenosine;
(Compound 85) $N^6$-1-(Acenaphthylenyl)methyl-2'-O-methyladenosine;
(Compound 86) $N^6$-(1,2-Dihydro-1-acenaphthylenyl)methyl-2'-O-methyladenosine;
(Compound 87) $N^6$-(2,3-Dihydro-1H-inden-1-yl)-2'-O-methyladenosine;
(Compound 88) $N^6$-(2,3-Dihydro-1H-inden-2-yl)-2'-O-methyladenosine;
(Compound 89) $N^6$-(2,3-Dihydro-1H-inden-1-yl)methyl-2'-O-methyladenosine;
(Compound 90) $N^6$-(3H-Inden-1-yl)methyl-2'-O-methyladenosine;
(Compound 91) $N^6$-(5-Methoxy-2,3-dihydro-1H-inden-2-yl)-2'-O-methyladenosine;
(Compound 92) $N^6$-(1-Tertrahydronaphtyl)-2'-O-methyladenosine;
(Compound 93) $N^6$-(2-Tertrahydronaphtyl)-2'-O-methyladenosine;
(Compound 94) $N^6$-(3,4-Dihydro-1-naphthyl)methyl-2'-O-methyladenosine;
(Compound 95) $N^6$-(5-Hydroxy-1-tetrahydronaphthyl)-2'-O-methyladenosine;
(Compound 96) $N^6$-(1-Hydroxy-1-tetrahydronaphthyl)-methyl-2'-O-methyladenosine;
(Compound 97) $N^6$-(5-Methoxy-1-tetrahydronaphthyl)-2'-O-methyladenosine;
(Compound 98) $N^6$-(6-Methoxy-1-tetrahydronaphthyl)-2'-O-methyladenosine;
(Compound 99) $N^6$-(7-Methoxy-1-tetrahydronaphthyl)-2'-O-methyladenosine;
(Compound 100) $N^6$-(4-Chromanyl)-2'-O-methyladenosine;
(Compound 101) $N^6$-(4-Thiochromanyl)-2'-O-methyladenosine;
(Compound 102) $N^6$-Fluorenyl-2'-O-methyladenosine;
(Compound 103) $N^6$-(9-Fluorenyl)methyl-2'-O-methyladenosine;
(Compound 104) $N^6$-(9-Hydroxy-9-fluorenyl)methyl-2'-O-methyladenosine; and
(Compound 105) $N^6$-(9-Xanthenyl)methyl-2'-O-methyladenosine.

The compounds of the present invention as given above may be prepared by a method disclosed, for example, in U.S. Pat. No. 4,843,066 and corresponding Japanese Laid Open (Kokai) No. 63/239,294, U.S. Pat. No. 4,985,409 and corresponding Japanese Laid Open (Kokai) No. 02/184,696, and Great Britain Patent No. 2,226,027A and corresponding Japanese Laid Open (Kokai) No. 02/218,689.

For example, the adenosine derivatives of the present invention can be prepared as follows:

(1) Adenosine or adenosine derivatives having a lower alkyl group, an amino group or halogen at the 2-position may be alkylated at the 2'-O- or 3'-O-position by an alkylating agent to give the compounds of the present invention. A diazoparaffin, such as diazomethane, diazoethane, diazopropane or diazobutane, can be used as the alkylating agent. The appropriate solvent which does not inhibit the reaction such as 1,2-dimethoxyethane can be preferably used. This O-alkylating reaction can be carried out as follows: (i) The reaction mixture is reacted for several minutes to several hours at room temperature in the presence of a catalyst such as p-toluenesulfonic acid; (ii) The starting material is dissolved in about 80° C. hot water and the alkylating agent such as diazoparaffin is added thereto, and the reaction mixture is reacted for several hours to a day.

(2) Both 3'-O- and 5'-O-positions of the adenosine derivatives are protected by tetraisopropyldisiloxane (TIPDS) group to carry out O-alkylation selectively at the 2'-O-position. A 6-chloropurine-9-riboside and TIPDSCL$_2$ (1,3-dichloro-1,1,3,3-tetraisopropyldisiloxane dichloride) are stirred for several hours at room temperature to protect the 3'-O- and 5'-O-positions, and then the 2'-O-position of the compound protected by TIPDS can be selectively alkylated by an alkylating agent such as methyl iodide, ethyl iodide, propyl iodide or butyl iodide in the presence of a catalyst such as silver oxide. After the 2'-O-alkylation, an amination or alkylamination at the 6-position can be carried out by reacting with ammonia or an alkylamine such as methylamine, ethylamine, propylamine or butylamine with heating. The protecting group, TIPDS, can be removed by a conventional method to give the compounds of the present invention.

(3) In the similar manner, both 2'-O- and 3'-O-positions of the adenosine derivatives are protected by isopropylidene group to carry out O-alkylation selectively at the 5'-O-position. Namely, a 6-chloropurine-9-riboside and 2,2-dimethoxypropane are reacted for several hours at room temperature in the presence of a catalyst such as p-toluenesulfonic acid to carry out isopropylidenation. After the 5'-O-alkylation, an amination or alkylamination at 6-position can be carried out as mentioned above. The protecting group, isopropylidene group, can be removed by a conventional method, for example, treatment with formic acid, to give the compounds of the present invention.

The resulting compounds of the present invention can be purified by known methods such as distillation chromatography and recrystallization. Identification is established through, inter alia, melting point, elemental analysis, IR, NMR, UV, mass spectrum, etc.

Adenosine derivatives of the present invention include the pharmaceutically acceptable salts of the compounds represented by the general formula. Examples of such salts are acid addition salts such as salts of hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid and sulfanilic acid and salts with alkali metal (e.g. sodium and potassium), alkali earth metal (e.g. calcium and magnesium) and metal (e.g. aluminum).

Adenosine derivatives of the present invention include metal complexes thereof such as, for example, complexes with zinc, nickel, cobalt, copper and iron.

These salts and metal complexes may be manufactured from free adenosine derivatives of the present invention or may be transformed each other.

When there are stereoisomers for the compounds of the present invention such as cis-trans isomers, optical isomers and conformational isomers, the present invention includes all of them.

The following descriptions serve to illustrative examples for preparation of the compounds of the present invention:

EXAMPLE 1

10 g of 6-chloro-9-(3,5-O-TIPDS)-β-D-ribofuranosyl-9H-purine was dissolved in 50 ml of ethyl iodide, and silver oxide was added and stirred with heating. The reaction mixture was applied on silica gel column, washed with benzene and then eluted with ethyl acetate/hexane. The eluate was concentrated to dryness under reduced pressure.

The residue was dissolved in benzene and a 40% (W/V) aqueous solution of monomethylamine was added thereto. After stirring overnight, the benzene layer was separated, washed with 1N HCl and brine, and a mixture of 1M tetra-n-butylammonium and tetrahydrofuran was added thereto. The reaction mixture was stirred for 30 minutes at room temperature concentration under reduced pressure, and then purified by silica gel column to give 2.1 g of $N^6$-methyl-2'-O-ethyladenosine (Compound 21).

$^1$H-NMR (D$_2$O): 1.21(3H,t), 3.19(3H,s), 3.58(1H,m), 3.69(1H,m), 3.85(1H,dd), 3.93(1H,dd), 4.32(1H,m), 4.55(1H,dd), 4.63(1H,dd), 6.10(1H,dd), 8.25(1H,s), 8.30(1H,s)

In the same manner as mentioned above, the following compounds were obtained.

$N^6$-Methyl-2'-O-n-butyladenosine (Compound 22)

$^1$H-NMR (DMSO-d$_6$): 0.74(3H,t), 1.17(2H,m), 1.37(2H,m), 2.96(3H,s), 3.34(1H,m), 3.55(2H,m), 3.68(1H,m), 3.99(1H,m), 4.29(1H,m), 4.47(1H,m), 5.15(1H,d), 5.42(1H,m), 5.99(1H,d), 7.81(1H,s), 8.23(1H,s), 8.37(1H,s)

$N^6$-Methyl-2'-O-n-hexyladenosine (Compound 23)

$^1$H-NMR (CDCl$_3$): 0.86(3H,t), 1.16(8H,m), 1.40(2H,m), 3.21(3H,s), 3.34(1H,m), 3.48(1H,m), 3.75(1H,m), 3.97(1H,m), 4.36(1H,m), 4.53(1H,d), 4.82(1H,dd), 5.82(1H,d), 5.87(1H,s), 6.87(1H,dd), 7.76(1H,s), 8.37(1H,s)

$N^6$-Methyl-2'-O-n-octyladenosine (Compound 24)

$^1$H-NMR (CDCl$_3$): 0.86(3H,t), 1.16(8H,m), 1.24(2H,m), 1.41(2H,m), 3.21(3H,s), 3.33(1H,m), 3.49(1H,m), 3.76(1H,m), 3.97(1H,m), 4.36(1H,m), 4.53(1H,d), 4.82(1H,dd), 5.82(1H,d), 6.02(1H,s), 6.87(1H,dd), 7.77(1H,s), 8.37(1H,s)

EXAMPLE 2

5.34 g of adenosine was dissolved in 80 ml of dimethylformamide and 800 mg of 60% W/W) sodium hydride in mineral oil was added thereto. After stirring for 30 minutes in ice-cold water, 2.84 g of methyl iodide in 10 ml of dimethylformamide was added dropwise. The reaction mixture was stirred under cooling for 2 hours and concentrated to dryness under reduced pressure. The residue was dissolved in water and applied on cation exchange column. The fraction was then eluted with 10% (V/V) aqueous solution of methanol collected, concentrated to dryness, and purified by silica gel column to give 1.36 g of 2',3'-O-dimethyladenosine.

m.p.: 180° C.

$^1$H-NMR (DMSO-d$_6$): 3.32(3H,s), 3.40(3H,s), 3.57(1H,m), 3.70(1H,m), 4.09(2H,m), 4.54(1H,dd), 5.47(1H,dd), 6.00(1H,d), 7.35(2H,s,D$_2$O-Disappearance), 8.14(1H,s), 8.38(1H,s)

EXAMPLE 3

2 g of the compound obtained in Example 2 and 2 ml of methyl iodide were dissolved in dimethylacetoamide, and stirred overnight at room temperature. The reaction mixture was concentrated to dryness under reduced pressure and 10 ml of 2N sodium hydroxide solution was added thereto. The solution was refluxed for one hour with heating. After cooling to room temperature, the solution was neutralized with 2N HCl and applied on Amberlite XAD-7 column. The column was washed with water and eluted with 50% (V/V) aqueous solution of methanol. The eluate was concentrated to dryness under reduced pressure and recrystallized from ethyl acetate to give 1.8 g of $N^6$,2',3'-O-trimethyladenosine (Compound 60).

m.p.: 165° C.

$^1$H-NMR (DMSO-d$_6$): 2.96(3H,s), 3.31(3H,s), 3.40(3H,s), 3.57(1H,m), 3.70(1H,m), 4.09(2H,m), 4.54(1H,dd), 5.49

(1H,dd), 6.01(1H,d), 7.83 (1H,s,D$_2$O-Disappearance), 8.24 (1H,s), 8.38(1H,s)

EXAMPLE 4

14.3 g of 6-chloro-9-β-D-ribofuranosyl-9H-purine and 15 g of triphenylchlorosilane were dissolved in 500 ml of pyridine and stirred for one hour at room temperature. Pyridine was distilled away and the residue was dissolved in benzene. The benzene layer was washed with 1N HCl and brine, and then dried over sodium sulfate anhydride. The solvent was distilled off and the residue was recrystallized from a mixture of hexane and ethyl acetate to give 21.5 g of 6-chloro-9-15-O-triphenylsilyl-β-D-ribofuranosyl)-9H-purine.

5.45 g of the resulting product was dissolved in 50 ml of ethyl iodide and silver oxide was added thereto with heating. The reaction mixture was applied on silica gel column. The column was washed with benzene and eluted with a mixture of hexane and ethyl acetate. The eluate was concentrated to dryness under reduced pressure. The residue was dissolved in benzene and a 40% (W/V) aqueous solution of monomethylamine was added thereto. After stirring overnight, the benzene layer was collected, washed with 1N HCl and brine and purified by silica gel column to give 6-amino-9-(5-O-triphenylsilyl-β-D-ribofuranosyl)-9H-purine. The resulting product was dissolved in tetrahydrofuran and tetra-n-butylammonium floride in tetrahydrofurane was added thereto. After stirring for 30 minutes at room temperature, the solution was concentrated to dryness under reduced pressure and purified by silica gel column to give 600 mg of N$^6$-methyl-2',3'-O-diethyladenosine (Compound 61).

m.p.: amorphous $^1$H-NMR (MeOH-d$_4$): 1.07(3H,t), 1.22(3H,t), 3.08(3H,s), 3.48(1H,m), 3.58(1H,m), 3.65(2H,m), 3.70(1H,dd), 3.87 (2H,m), 4.20(1H,dd), 6.00(1H,d), 8.20(1H,s), 8.23(1H,s)

EXAMPLE 5

2-Methyladenosine was dialkylated in the same manner as Example 2 to give 2,2',3'-O-trimethyladenosine (Compound 63).

m.p.: 156° C.

$^1$H-NMR (DMSO-d$_6$): 2.39(3H,s), 3.28(3H,s), 3.40(3H, s), 3.58(1H,m), 3.70(1H,m), 4.08(1H,m), 4.13(1H,m), 4.52 (1H,m), 5.80(1H,m,D$_2$O-Disappearance),5.95(1H,d), 7.27 (2H,s,D$_2$O-Disappearance), 8.28(1H,s)

EXAMPLE 6

Compound 63 was methylated by methyl iodide and then rearranged to give 2,N$^6$,2',3'-O-tetramethyladenosine (Compound 64).

$^1$H-NMR (DMSO-d$_6$): 2.43(3H,s), 2.94(3H,s), 3.28(3H, s), 3.40(3H,s), 3.57(1H,m), 3.70(1H,m), 4.08(1H,m), 4.13 (1H,m), 4.52(1H,m), 5.79(1H,m,D$_2$O-Disappearance), 5.96 (1H,d), 7.71(1H,s,D$_2$O-Disappearance), 8.26(1H,s)

EXAMPLE 7

1.2 g of 2-iodoadenosine was suspended in 150 ml of 1 mmol tin chloride dihydrate/methanol. 50 ml of 0.4–0.5M diazomethane in 1,2-dimethoxyethane was added with stirring. After stirring for one hour at room temperature, the reaction mixture was concentrated to dryness under reduced pressure. The resulting product was applied on ODS column and eluted with 40% (V/V) methanol in 0.1% (V/V) aqueous solution of TFA. First, 2-iodo-2'-O-methyladenosine (Compound 47) was eluted, and then 2-iodo-3'-O-methyladenosine (Compound 48) was eluted. Both fractions were concentrated to dryness to give 135 mg of Compound 47 and 56 mg of Compound 48.

2-iodo-2'-O-methyladenosine (Compound 47)

$^1$H-NMR (D$_2$O): 3.52(3H,s), 3.92(1H,dd), 3.97(1H,dd), 4.27(1H,m), 4.54(1H,dd), 4.61 (1H,dd), 6.02(1H,d), 7.98 (1H,s)

2-iodo-3'-O-methyladenosine (Compound 48)

$^1$H-NMR (D$_2$O): 3.58(3H,s) 3.86(1H,dd) 3.94(1H,dd), 4.18(1H,dd) 4.35(1H,m) 4.97(1H,dd) 5.93(1H,d), 7.94(1H, s)

In the same manner the following compounds were obtained by using 2-substitutedadenosine, N$^6$-substitutedadenosine or 2, N$^6$-disubstitutedadenosine.

2-Methoxy-3'-O-methyladenosine (Compound 9)

$^1$H-NMR (D$_2$O): 3.56(3H,s) 3.84(1H,dd), 3.94(1H,dd), 3.96(3H,s) 4.22(1H,dd) 4.33(1H,m) 5.06(1H,dd), 5.98(1H, d) 8.10(1H,s,8-H)

N$^6$,2'-O-Dimethyl-2-hexyladenosine (Compound 30)

$^1$H-NMR (MeOH-d$_4$): 0.88(3H,t) 1.33(6H,m), 1.78(2H, quintet), 2.74(2H,t), 3.12(3H,brs), 3.37(3H,s), 3.73(1H,dd), 3.88(1H,dd), 4.18(1H,m), 4.49(2H,m), 5.98(1H,d), 8.10(1H, s,8-H)

N$^6$,2'-O-Dimethyl-2-decyladenosine (Compound 31)

$^1$H-NMR (MeOH-d$_4$): 0.88(3H,t), 1.27–1.33(14H,m), 1.78(2H,quintet), 2.75(2H,t), 3.13(3H,brs), 3.37(3H,s), 3.73 (1H,dd), 3.89(1H,dd), 4.18(1H,m), 4.49(2H,m)

N$^6$,2'-O-Dimethyl-2-(1-hexyn-1-yl)adenosine (Compound 32)

$^1$H-NMR (MeOH-d$_4$): 0.97(3H,t), 1.52(2H,m), 1.62(2H, m), 2.54(2H,t), 3.09(3H,brs), 3.40(3H,s), 3.74(1H,dd), 3.88 (1H,dd), 4.15(1H,m), 4.42(1H,dd), 4.48(1H,dd), 6.00(1H, d), 8.22(1H,s)

N$^6$,2'-O-Dimethyl-2-(1-dodecyl-1-yl)adenosine (Compound 33)

$^1$H-NMR (MeOH-d$_4$): 0.89(3H,t), 1.30(14H,m), 1.49(2H, m), 1.63(2H,quintet), 2.43(2H,t), 3.41(3H,s), 3.74(1H,dd), 3.88(1H,dd), 4.15(1H,m), 4.41(1H,dd), 4.48(1H,dd), 6.00 (1H,d), 8.30(1H,s)

2-Phenyl-2'-O-methyladenosine (Compound 37)

$^1$H-NMR (MeOH-d$_4$): 3.53(3H,s), 3.77(1H,dd), 3.91(1H, dd), 4.12(1H,m), 4.50(1H,dd), 4.54(1H,dd), 6.20(1H,d), 7.43(3H,m), 8.32(2H,m), 8.36(1H,s)

2-Phenyl-3'-O-methyladenosine (Compound 38)

$^1$H-NMR (MeOH-d$_4$): 3.53(3H,s), 3.74(1H,dd), 3.88(1H, dd), 4.10(1H,dd), 4.22(1H,dd), 5.00(1H,dd), 6.07(1H,d), 7.42(3H,m), 8.32(3H,m)

2-Bromo-2'-O-methyladenosine (Compound 43)

$^1$H-NMR (D$_2$O): 3.50(3H,s), 3.91(1H,dd), 3.99(1H,dd), 4.37(1H,m), 4.57(1H,dd), 4.67(1H,dd), 6.13(1H,d), 8.37 (1H,s)

2-Bromo-3'-O-methyladenosine (Compound 44)

$^1$H-NMR (D$_2$O): 3.60(3H,s), 3.90(1H,dd), 4.01(1H,dd), 4.19(1H,dd), 4.44(1H,m), 4.95(1H,dd), 6.07(1H,d), 8.37 (1H,s)

2-Bromo-N$^6$,2'-O-dimethyladenosine (Compound 45)

$^1$H-NMR (D$_2$O): 3.22(3H,s), 3.57(3H,s), 3.90(1H,dd), 3.98(1H,dd), 4.29(1H,m), 4.59(1H,dd), 4.65(1H,dd), 6.12 (1H,d), 8.16(1H,s)

2-Bromo-N$^6$,3'-O-dimethyladenosine (Compound 46)

$^1$H-NMR (D$_2$O): 3.07(3H,s), 3.60(3H,s), 3.93(1H,dd), 3.99(1H,dd), 4.23(1H,dd), 4.36(1H,m), 5.03(1H,dd), 6.03 (1H,d), 8.14(1H,s)

2-Pentylamino-2'-O-methyladenosine (Compound 52)

$^1$H-NMR (MeOH-d$_4$): 0.94(3H,t), 1.38(4H,m), 1.65(2H, m), 3.42(2H,t), 3.49(3H,s), 3.76(1H,dd), 3.87(1H,dd), 4.08 (1H,m), 4.25(1H,t), 4.43(1H,t), 5.99(1H,d), 8.22(1H,s)

2-Phenylamino-2'-O-methyladenosine (Compound 53)

¹H-NMR (MeOH-d₄): 3.46(3H,s), 3.74(1H,dd), 3.85(1H, dd), 4.07(1H,m), 4.23(1H,dd), 4.39(1H,dd), 6.03(1H,d), 7.11(1H,t), 7.35(2H,t), 7.60(2H,d), 8.35(1H,s)

2-Phenylamino-3'-O-methyladenosine (Compound 54)

¹H-NMR (MeOH-d₄): 3.46(3H,s), 3.69(1H,dd), 3.79(1H, dd), 3.94(1H,dd), 4.16(1H,m), 4.74(1H,dd), 5.91(1H,d), 7.13(1H,t), 7.36(2H,t), 7.60(2H,d), 8.28(1H,s)

2-Phenylamino-N⁶,2'-O-dimethyladenosine (Compound 55)

¹H-NMR (MeOH-d₄): 3.16(3H,s), 3.47(3H,s), 3.77(1H, dd), 3.88(1H,dd), 4.11(1H,m), 4.20(1H,dd), 4.40(1H,dd), 6.06(1H,d), 7.12(1H,t), 7.35(2H,t), 7.63(2H,d), 8.42(1H,s)

2-Phenylamino-N⁶,3'-O-dimethyladenosine (Compound 56)

¹H-NMR (MeOH-d₄): 3.10(3H,s), 3.49(3H,s), 3.72(1H, dd), 3.85(1H,dd), 3.98(1H,dd), 4.17(1H,m), 4.85(1H,dd), 5.88(1H,d), 6.94(1H,t), 7.26(2H,t), 7.69(2H,d), 7.99(1H,s)

2-(3-Hydroxy-1-propyn-1-yl)-2'-O-methyladenosine (Compound 57)

¹H-NMR (D₂O): 3.45(3H,s), 3.86(1H,dd), 3.95(1H,dd), 4.32(1H,m), 4.51 (1H,dd), 4.52(2H,s), 4.62(1H,dd), 6.08 (1H,d), 8.30(1H,s)

2-(3-Hydroxy-1-propyn-1-yl)-3'-O-methyladenosine (Compound 58)

¹H-NMR (D₂O+MeOH-d₄): 3.51(3H,s), 3.80(1H,dd), 3.92(1H,dd), 4.09(1H,m), 4.36(1H,m), 4.47(2H,s), 4.83(1H, dd), 5.96(1H,d), 8.30(1H,s)

EXAMPLE 8

2.2 g of AICA-2'-O-methylriboside was dissolved in 20 ml of dimethylformamide and 1.7 g of benzoylisothiocyanate was added thereto. After stirring for 3 hours at room temperature, 3.3 g of dicyclohexylcarbodiimide was added and reacted for 20 hours at room temperature. The reaction mixture was concentrated to an oily residue. To the residue, 50 ml of ethanol and 50 ml of aqua ammonia were added, and stirred for 18 hours at room temperature.

The resulting precipitate was collected by filtration to give 1.7 g of 2-hydroxy-2'-O-methyladenosine (Compound 39).

¹H-NMR (D₂O): 3.46(3H,s), 3.82(1H,dd), 3.90(1H,dd), 4.27(1H,m), 4.50(1H,dd), 4.59(1H,dd), 5.95(1H,d), 8.03 (1H,s)

In the same manner, AICA-3'-O-methylriboside was used as a starting material to give 2-hydroxy-3'-O-methyladenosine (Compound 40).

¹H-NMR (D₂O): 3.54(3H,s), 3.82(1H,dd), 3.94(1H,dd), 4.10(1H,dd), 4.36(1H,m), 4.86(1H,dd), 5.89(1H,dd), 8.03 (1H,s)

The following descriptions serve to illustrate pharmaceutical studies of the compounds of the present invention.

1. Adenosine Deaminase Inhibiting Action

The enzymatic reaction was conducted at 25° C. in a 0.05M phosphate buffer (pH=7.5). Thus, a reaction solution comprising 800 μl of substrate solution (adenosine), 100 μl of a solution to be tested and 100 μl of enzyme solution (adenosine deaminase of type VII; mucous membrane of intestinal tract of calf) was reacted for 5 minutes and the reaction was stopped by adding 100 μl of acetic acid. Then the amount of inosine produced was determined by means of an HPLC to measure the inhibiting activity. The test was conducted for various substrate concentrations and Ki values were measured by Lineweaver-Burk plots.

Examples of the results are given in Table 1.

TABLE 1

| Compound Tested | Ki Value (M) |
|---|---|
| 1 | $1.31 \times 10^{-5}$ |
| 2 | $4.93 \times 10^{-4}$ |
| 4 | $3.47 \times 10^{-6}$ |
| 5 | $2.46 \times 10^{-5}$ |
| 6 | $1.79 \times 10^{-4}$ |
| 18 | $1.24 \times 10^{-6}$ |
| 19 | $7.78 \times 10^{-5}$ |
| 20 | $2.69 \times 10^{-4}$ |
| 21 | $3.30 \times 10^{-7}$ |
| 22 | $5.58 \times 10^{-8}$ |
| 23 | $8.90 \times 10^{-7}$ |
| 24 | $1.10 \times 10^{-7}$ |
| 25 | $3.59 \times 10^{-4}$ |
| 27 | $8.59 \times 10^{-7}$ |
| 30 | $9.00 \times 10^{-8}$ |
| 31 | $2.80 \times 10^{-7}$ |
| 32 | $1.20 \times 10^{-7}$ |
| 33 | $1.50 \times 10^{-5}$ |
| 34 | $3.59 \times 10^{-4}$ |
| 37 | $6.60 \times 10^{-7}$ |
| 38 | $7.90 \times 10^{-6}$ |
| 39 | $1.90 \times 10^{-5}$ |
| 43 | $3.20 \times 10^{-6}$ |
| 44 | $2.20 \times 10^{-5}$ |
| 45 | $1.20 \times 10^{-7}$ |
| 46 | $3.70 \times 10^{-6}$ |
| 47 | $2.30 \times 10^{-7}$ |
| 48 | $4.40 \times 10^{-6}$ |
| 50 | $2.80 \times 10^{-5}$ |
| 51 | $5.00 \times 10^{-6}$ |
| 52 | $6.00 \times 10^{-7}$ |
| 53 | $1.70 \times 10^{-7}$ |
| 54 | $2.20 \times 10^{-6}$ |
| 55 | $1.30 \times 10^{-8}$ |
| 56 | $1.10 \times 10^{-7}$ |
| 57 | $3.00 \times 10^{-5}$ |
| 59 | $7.50 \times 10^{-6}$ |
| 60 | $7.50 \times 10^{-7}$ |
| 61 | $1.50 \times 10^{-7}$ |
| 63 | $1.30 \times 10^{-6}$ |
| 64 | $8.80 \times 10^{-7}$ |
| 73 | $1.03 \times 10^{-3}$ |

2. Therapeutic Action to Nephritis.

When puromycin aminonucleoside is administered to rats, symptoms similar to protein-rich urine, hypoproteinemia, hyperlipemia, nephrotic syndrome, etc. result and, therefore, rats which are administered with puromycin aminonucleoside have been used as pathological model animals for nephritis. The chemical name for puromycin aminonucleoside is 3'-amino-3'-deoxy-N,N-dimethyladenosine. A method by Endo, et al. [Sogo Rinsho, vol. 38, no. 5, page 821 (1989)] was somewhat modified and used as a test method here. Thus, a solution of puromycin aminonucleoside was dissolved in a physiological saline liquid and administered just once to a tail vein of a male rat (SD strain) of about 200 g body weight at a dose of 100 mg/kg (the initial of zero-th day).

The compound to be tested was dissolved in a physiological saline liquid and was given orally for five consecutive days from the zero-th day at a dose of 50 mg/kg each. After 24 hours, the accumulated urine was collected and the amount of urine and the amount of protein in the urine was measured. Blood was collected on the tenth day and the total protein in serum, creatinine in serum and urea nitrogen were measured.

Examples of the results are given in Tables 2 and where the control is those animals injected only with the puromycin aminonucleoside:

TABLE 2

| Compound to be Tested | Urea Nitrogen (mg/dl) | Total Protein in Serum (g/dl) | Serum Creatinine (mg/dl) |
|---|---|---|---|
| Normal | 17.6 | 7.90 | 0.38 |
| Control | 40.0 | 7.08 | 0.85 |
| Compound 27 | 31.9 | 7.44 | 0.71 |

TABLE 3

Amount of Protein in Urine (mg/day)

| Days | Control | Compound 27 |
|---|---|---|
| 1st Day | 0 | 0 |
| 2nd | 32.0 | 29.2 |
| 3rd | 44.7 | 33.8 |
| 4th | 173.4 | 122.5 |
| 5th | 522.5 | 399.8 |
| 6th | 704.1 | 443.7 |
| 7th | 826.5 | 558.7 |
| 8th | 811.6 | 595.6 |
| 9th | 814.0 | 593.5 |
| 10th | 684.0 | 528.6 |

3. Inhibitory Action against Activated Oxygen Generation

Human peripheral polymorphonuclear leukocyte (PML, $2\times10^6$ cells) prepared in a conventional method, bovine heart cytochrome C type-III (75 nmol), cytocharasin (5 μg) and tested drug were mixed with HEPES-buffered saline solution (final 1 ml) and incubated for 5 minutes at 37° C. N-Formyl-methionyl-leucyl-phenylalanine (FMLP) was added (final $10^{-7}$M) and incubated for 5 minutes. Immediately after the incubation, the reaction mixture was centrifuged at 4° C., and then the absorbance at 550 nm of the supernatant was measured with a spectrophotometer.

An excess amount of bovine liver superoxide dismutase (SOD) was added to the reaction mixture and the absorbance of the supernatant was also measured in the same manner as above as a blank value.

A portion of adenosine deaminase (ADA) may be removed during the preparation of human peripheral PML. Therefore, the inhibitory action against the generation of superoxide of the tested drug was measured in the same manner as mentioned above, adding 0.02 units of bovine liver ADA with human peripheral PML.

The inhibition against superoxide generation was calculated by the following equation, and examples of the results are given in Table 4.

$$\text{Inhibition \%} = \left(1 - \frac{\text{Drug A}_{550} - \text{SOD A}_{550}}{\text{Control A}_{550} - \text{SOD A}_{550}}\right) \times 100$$

TABLE 4

| Without ADA | | With ADA | |
|---|---|---|---|
| Compound 27 (M) | Inhibition | Compound 27 (M) | Inhibition |
| $1 \times 10^{-3}$ | 100% | $1 \times 10^{-4}$ | 88% |
| $1 \times 10^{-4}$ | 79% | $1 \times 10^{-5}$ | 77% |
| $1 \times 10^{-5}$ | 22% | $1 \times 10^{-6}$ | 34% |
| $1 \times 10^{-6}$ | 2% | $1 \times 10^{-7}$ | 10% |

4. Suppressive Action against Ischemic Edema

The right hind paw of ICR-strain male mice (11 weeks of age) were fastened with a rubber band to stop the blood stream for 20 minutes, and then the rubber band was removed to recover the blood stream. The tested drug was administered intravenously before the treatment. Each of the right and left hind paws were weighed and the suppressive action was measured according to the weight difference between the treated and untreated paws.

Examples of the results are given in Table 5.

TABLE 5

| Tested Drug (10 mg/kg) | Paw Weight (mg) | | Inhibition (%) |
|---|---|---|---|
| | Treated | Untreated | |
| Control | 314.8 ± 6.8 | 219.9 ± 6.2 | — |
| Compound 27 | 254.4 ± 6.6 | 223.86.2 | 67.7 |
| Allopurinol | 283.2 ± 6.3 | 222.9 ± 6.9 | 36.4 |

5. Effect on the Concentrations of Adenosine and Inosine

Human peripheral polymorphonuclear leukocyte ($2\times10^6$ cells), cytochalasin (5 μg) and the tested drug were mixed with HEPES-buffered saline solution (final 0.5 ml) and incubated for 5 minutes. FMLP was added (final $10^{-7}$M) and incubated for 10 minutes. As a result of HPLC analyses of the reaction mixture, in FMLP-treated group, the inosine peak increased compared to the control group. The compound of the present invention was added to the FMLP-treated group, which showed a decrease in the inosine peak and a significant increase in the adenosine peak compared with the group when the compound of the present invention was not added.

As shown in Table 1, the compounds of the present invention exhibit excellent adenosine deaminase inhibiting action. Adenosine deaminase which is a metabolic enzyme for adenosine is inhibited whereby the adenosine concentration in tissues increases. Neutrophils produce activated oxygen when the tissue is in an ischemic state. Adenosine inhibits the production of activated oxygen and, in addition, adenosine directly eliminates the produced activated oxygen. Further, adenosine lowers the inosine concentration whereby it decreases the supply of hypoxanthine. Hypoxanthine is a substrate of xanthine-xanthineoxidase system. The xanthine-xanthineoxidase system is one of the systems producing the activated oxygen. Adenosine deaminase inhibiting substance having a production inhibiting action and an eliminating action for activated oxygen source as such shows pharmacological actions such as improvement of coronary and cerebral blood vessel circulation, prevention and therapy of renal diseases, antiinflammatory activity, etc.

Further, as shown in Tables 2 and 3, the compounds of the present invention having adenosine deaminase inhibiting action were evaluated by means of pharmacological experiments. Rats which had been administered with puromycin aminonucleoside were used as pathological model animals for nephritis. Indexes such as total protein in serum, creatinine in serum and urea nitrogen concentrations were used to evaluate the therapeutic effects of the instant compounds.

Consequently, the compounds of the present invention having adenosine deaminase inhibiting action are useful as pharmaceuticals for the prevention and therapy of various kinds of diseases such as ischemic heart diseases, diseases caused by cerebrovascular disorder, renal diseases, and allergic diseases. Examples of ischemic heart diseases which may be treated include angina pectoris, myocardial infarction and arrhythmia. Exemplary of diseases caused by cerebrovascular disorder which may be treated are cerebral hemorrhage, cerebral infarction, cerebral apoplexy and cerebral arteriosclerosis. Nephritis and renal failure are examples of renal diseases which may be treated and examples of allergic diseases which may be treated include asthma, allergic rhinitis, allergic conjunctivitis, urticaris and rheumatism. Moreover, the compounds of the present invention are very useful as pharmaceuticals for the prevention and therapy of post-operative complicated diseases because they inactivate activated oxygen which is generated in ischemic areas during the recirculation of blood after operations.

Adenosine analogs such as 3'-deoxyadenosine and xylosyladenine (anticancer drugs) and arabinosyladenine (exhibiting antiherpes activity) are easily deaminated by adenosine deaminase in vivo and are inactivated. Accordingly, when the compounds of the present invention having adenosine deaminase inhibiting action are administered before or together with administration of the above-mentioned anticancer drugs or antiviral drugs, an effect of inhibiting the decrease in action of such adenosine analogous anticancer and antiviral drugs can be expected as well. For the purposes of this invention, an adenosine analogous drug is defined as a drug which is metabolized or deaminated by adenosine deaminase.

Adenosine has many pharmacological activities such as cardiovasodilating or platelet-aggregation inhibiting activity, so adenosine is used to improve blood circulation and treat heart failure, myocardial infarction and other such conditions. Adenosine is metabolized by adenosine deaminase and is consequently inactive. Accordingly, when the compounds of the present invention are administered before or together with the administration of adenosine, the instant compounds may inhibit the decrease in such action of adenosine.

The compounds of the present invention can be made into pharmaceuticals by combining them with suitable carriers or diluents. The compounds of the present invention can also be made into pharmaceutical preparations by any of the conventional methods giving solid, semisolid, liquid or gaseous forms for oral or parenteral administration.

In manufacturing such preparations, the compounds of the present invention may be used in the form of their pharmaceutically acceptable salts. The compounds of the present invention may be used either solely or jointly in the form of a suitable combination. Alternatively, the compounds may be compounded with other pharmaceutically active components.

In the case of oral preparations, the compounds of the present invention may be used alone or combined with appropriate additives to make tablets, diluted powders, granules or capsules. The compounds may be combined with conventional fillers such as lactose, mannitol, corn starch, and potato starch; binders such as crystalline cellulose, cellulose derivatives, gum arabic, corn starch and gelatin; lubricants such as talc and magnesium stearate; disintegrators such as corn starch, potato starch or sodium carboxymethylcellulose; and if desired with diluents, buffering agents, extenders, moisturizers, preservatives, flavoring agents and perfumes.

Alternatively, the compounds of the present invention may be made into a suppository by mixing with a variety of bases. Exemplary bases include fatty and oil bases such as cocoa butter, emulsifying bases, water-soluble bases such as Macrogol and hydrophilic bases.

In the case of injections, the compounds may be dissolved, suspended or emulsified in aqueous solvents or nonaqueous solvents. Examples of aqueous and nonaqueous solvents include distilled water, physiological saline liquid, Ringer solution and solutions containing plant oil, synthetic fatty acid glycerides, vegetable oil, higher fatty acid esters and propylene glycol.

Further, depending upon the state of the patient, or the type of the disease, the compounds may be made into other preparation forms which are most suitable for the therapy such as inhalants, aerosols, ointments, poultices and eye drops. In the case of inhalations or aerosol preparations, the compounds of the invention in the form of a liquid or a minute powder can be filled up in an aerosol container with gas or a liquid spraying agent, and if desired, with conventional adjuvants such as humidifying agents or dispersing agents.

Cataplasms can be prepared by mixing the compounds with mentha oil, concentrated glycerin, kaolin or other such additives.

The desired doses of the compounds of the present invention vary depending upon the patient to be treated, the preparation form, the method of administration, and the period of administration. In general, 0.1 to 5,000 mg or, preferably, 0.2 to 3,000 mg per day may be given to an adult by oral route for achieving the desired effect.

In the case of parenteral administrations such as injections, doses of the compounds on the order of one third to one tenth of the above dose are preferable as daily doses.

It is claimed:

1. An adenosine derivative represented by the following formula or a pharmaceutically acceptable salt thereof:

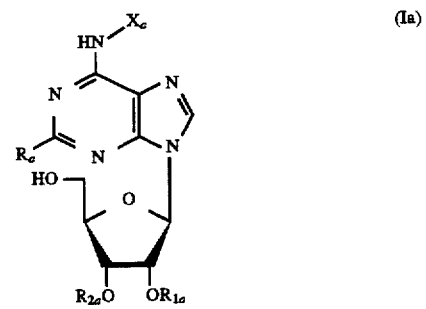

wherein each of $R_1a$, $R_2a$ and Xa may be the same or different and is hydrogen or alkyl, at least one of $R_1a$ and $R_2a$ being an alkyl; and Ra is an alkyl having more than 6 carbons, alkenyl, alkynyl, hydroxyalkynyl, alkoxy, phenyl, hydroxy, alkylamino or phenylamino.

2. An adenosine derivative represented by the following formula or a pharmaceutically acceptable salt thereof:

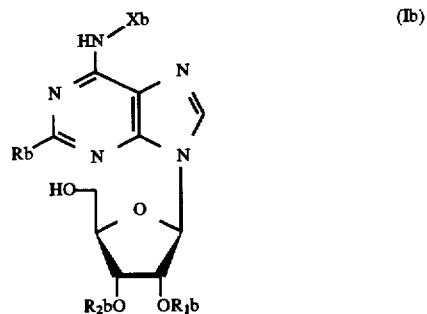

wherein $R_1b$ and $R_2b$ are the same and each is methyl or ethyl;

Rb and Xb is hydrogen or methyl; and at least one of Rb and Xb is methyl.

3. An adenosine derivative represented by the following formula or a pharmaceutically acceptable salt thereof:

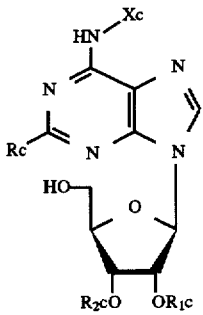

(Ic)

wherein one of $R_1c$ and $R_2c$ is methyl and the other is hydrogen;

when Xc is hydrogen, Rc is iodo; and when Xc is methyl, Rc is bromo or iodo.

4. An adenosine derivative represented by the following formula or a pharmaceutically acceptable salt thereof:

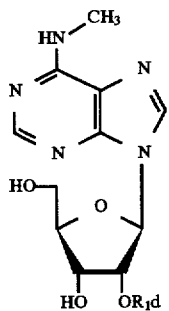

(Id)

wherein $R_1d$ is an alkyl having 2 to 8 carbons.

5. An adenosine derivative as claimed in claim 1 wherein $R_1a$ is alkyl.

6. An adenosine derivative as claimed in claim 3 wherein $R_1c$ is methyl.

7. A pharmaceutical composition comprising:

(a) at least one adenosine deaminase inhibitor comprising at least one of the compounds represented by the formula (I) or a pharmaceutically effective salt thereof:

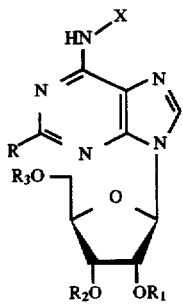

(I)

wherein each of $R_1$, $R_2$ and $R_3$ may be the same or different and $R_1$, $R_2$ and $R_3$ is hydrogen or alkyl, at least one of $R_1$, $R_2$ and $R_3$ being an alkyl;

R is hydrogen, alkyl, alkenyl, alkynyl, hydroxyalkynyl, alkoxy, phenyl, hydroxy, amino, alkylamino, phenylamino or halogen; and X is hydrogen, alkyl, alkynyl, allyl, methallyl, cycloalkyl, an alkyl having one or more hydroxy groups, phenyl, substituted phenyl, alkyl having one or more phenyl groups, alkyl having one or more substituted phenyl groups, bicycloalkyl, naphthalkyl, acenaphthylenylalkyl or a group represented by Formula (II) or Formula (III):

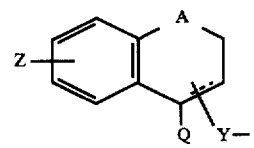

(II)

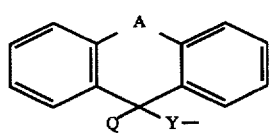

(III)

wherein Z is hydrogen, hydroxy or lower alkoxy;

Q is hydrogen or hydroxy;

A is —$CH_2$—, —O—, —S— or a single bond forming a five-membered ring;

Y is —$(CH_2)_n$— or a single bond;

n is an integer from 1 to 3; and (b) adenosine or at least one therapeutically useful adenosine analogous drug which is different from (a) and which is metabolized or deaminated by adenosine deaminase;

as active ingredients wherein said adenosinedeaminase inhibitor inhibits loss of activity of said adenosine or said adenosine analogous drug.

8. The composition of claim 7 wherein said adenosine analogous drug is an anticancer drug, or an antiviral drug, or a combination of an anticancer drug with an antiviral drug.

9. The composition of claim 8 wherein said anticancer drug is 3'-deoxyadenosine or xylosyladenine and said antiviral drug is arabinosyladenine.

10. The composition of claim 7 wherein $R_3$ is hydrogen.

11. The composition of claim 10 wherein X is hydrogen.

12. The composition of claim 10 wherein X is an alkyl having 1 to 3 carbon atoms.

13. The composition of claim 7 wherein $R_1$ is an alkyl.

* * * * *